United States Patent
Tanno et al.

(10) Patent No.: US 7,227,646 B2
(45) Date of Patent: Jun. 5, 2007

(54) HIGH-SPEED OPTICAL DELAY GENERATING METHOD BY ROTATION REFLECTOR IN OPTICAL COHERENCE TOMOGRAPHY AND OPTICAL COHERENCE TOMOGRAPHY DEVICE

(75) Inventors: Naohiro Tanno, Yamagata (JP); Sumio Matsumura, Yamagata (JP); Michiro Hasegawa, Yamagata (JP); Yukinori Hino, Yamagata (JP); Tohru Nakagawa, Yamagata (JP); Masahiro Kohno, Yamagata (JP)

(73) Assignees: Japan Science and Technology Agency, Kawaguchi-shi (JP); MTEX Matsumura Corporation, Tendo-shi (JP)

( * ) Notice: Subject to any disclaimer, the term of this patent is extended or adjusted under 35 U.S.C. 154(b) by 252 days.

(21) Appl. No.: 10/474,341

(22) PCT Filed: Apr. 11, 2002

(86) PCT No.: PCT/JP02/03606

§ 371 (c)(1),
(2), (4) Date: Oct. 8, 2003

(87) PCT Pub. No.: WO02/084259

PCT Pub. Date: Oct. 24, 2002

(65) Prior Publication Data
US 2004/0114151 A1 Jun. 17, 2004

(30) Foreign Application Priority Data
Apr. 13, 2001 (JP) ............................. 2001-114898

(51) Int. Cl.
*G01B 9/02* (2006.01)

(52) U.S. Cl. ....................... 356/497; 356/479

(58) Field of Classification Search ................ 356/479, 356/484, 485, 487, 489, 497
See application file for complete search history.

(56) References Cited

U.S. PATENT DOCUMENTS
5,321,501 A * 6/1994 Swanson et al. ............. 356/479

(Continued)

FOREIGN PATENT DOCUMENTS
JP      56-129826      10/1981

(Continued)

OTHER PUBLICATIONS

Boscher, C., et al, "Vitrectomy with endoscopy for management of retained lens fragments and/or posteriorly dislocated intraocular lens," Graefe's Arch Clin Ophthalmol 236: pp. 115-121 (1998).*

*Primary Examiner*—Layla G. Lauchman
*Assistant Examiner*—Marissa J. Detschel
(74) *Attorney, Agent, or Firm*—Oblon, Spivak, McClelland, Maier & Neustadt, P.C.

(57) ABSTRACT

A high-speed optical delay generating method by a rotation reflector in optical coherence tomography, capable of providing a sectional picture with a sufficiently long depth-direction (Z direction) scanning distance, and an optical coherence tomography device therefor are provided. The device comprises a low-coherence light source (1), a half mirror (2) for splitting light from the low-coherence light source (1) into two, that is, into object light towards an object (A) to be examined and reference light, a light delay mechanism (3) for delaying the reference light by means of a rotation reflector (12), a fixed mirror (4) for reflecting/returning the reference light from the light delay mechanism (3), the half-mirror (2) for combining the object light returning from the object (A) to be examined with the reference light returning from the light delay mechanism, and a light detector (11) for detecting interference light including a heterodyne interference beat signal combined at the half mirror (2).

6 Claims, 2 Drawing Sheets

U.S. PATENT DOCUMENTS

| | | | |
|---|---|---|---|
| 6,057,920 A * | 5/2000 | Fercher et al. | 356/497 |
| 6,124,929 A * | 9/2000 | Weibel | 356/451 |
| 6,137,585 A * | 10/2000 | Hitzenberger et al. | 356/484 |
| 6,501,551 B1 * | 12/2002 | Tearney et al. | 356/477 |
| 6,741,359 B2 * | 5/2004 | Wei et al. | 356/512 |

FOREIGN PATENT DOCUMENTS

| | | |
|---|---|---|
| JP | 7-49306 | 2/1995 |
| JP | 7-265316 | 10/1995 |
| JP | 2001-228080 | 8/2001 |

* cited by examiner

HIGH-SPEED OPTICAL DELAY GENERATING METHOD BY ROTATION REFLECTOR IN OPTICAL COHERENCE TOMOGRAPHY AND OPTICAL COHERENCE TOMOGRAPHY DEVICE

TECHNICAL FIELD

The present invention relates to a high-speed optical delay generating method by a rotation reflector in optical coherence tomography, and to an optical coherence tomography device therefor.

BACKGROUND ART

As a conventional high-speed optical delay generating method in optical coherence tomography, a method has been known, in which the light-path for reference light extends through a half mirror, a first mirror, a second mirror, and the half mirror, and the boundary between the first mirror and the second mirror is set to be the reflection center.

FIG. 1 schematically shows the configuration of a conventional optical coherence tomography device. This figure shows a low-coherence light source (e.g., an SLD (super luminescent diode) light source) 101, a half mirror (two-splitting half mirror) 102, a rotating member 103, a first mirror 104A, a second mirror 104B, mirrors 105 and 106, an object A to be examined, and a light detector 107.

DISCLOSURE OF INVENTION

However, according to the above-described conventional high-speed optical delay generating method in optical coherence tomography, the reflection optical axis is shifted with respect to the incident optical axis, depending on the rotation angle, whenever scanning is carried out in the depth direction (Z direction). Thus, heterodyne interference beat signals combined at the two-splitting half mirror can be obtained only in a very small angular range.

Accordingly, the optical coherence tomography device using the conventional high-speed optical delay generating method in optical coherence tomography has a problem in that only cross-sectional pictures having a very short scanning-distance in the depth direction (Z direction) can be provided.

In view of the foregoing, it is an object of the present invention to provide a high-speed optical delay generating method by a rotation reflector in optical coherence tomography, capable of providing a sectional picture with a sufficiently long depth-direction (Z direction) scanning distance, and an optical coherence tomography device therefor.

To achieve the object of the present invention:

[1] a high-speed optical delay generating method by a rotation reflector in optical coherence tomography comprises splitting light from a low-coherence light source into two, that is, into object light towards an object to be examined and reference light by means of a two-splitting half mirror, causing the reference light to be reflected at and return from a fixed mirror via a light delay mechanism containing the rotation reflector to be combined with the object light returning from the object to be examined at the two-splitting half mirror, and detecting interference light including a heterodyne interference beat signal combined at the two-splitting half mirror;

[2] an optical coherence tomography device comprises a low-coherence light source, a two-splitting half mirror for splitting light from the low-coherence light source into two, that is, into object light towards an object to be examined and reference light, a light delay mechanism for delaying the reference light by means of a rotation reflector, a fixed mirror for causing the reference light from the light delay mechanism to be reflected thereat and return therefrom, the two-splitting half mirror for combining the object light returning from the object to be examined with the reference light returning from the light delay mechanism, and a light detector for detecting interference light including a heterodyne interference beat signal combined at the two-splitting half mirror;

[3] an optical coherence tomography device comprises a low-coherence light source, a two-splitting half mirror for splitting light from the low-coherence light source into two, that is, into object light towards an object to be examined and reference light, a light delay mechanism for delaying the reference light by means of a rotation reflector, a fixed mirror for causing the reference light from the light delay mechanism to be reflected thereat and return therefrom, a plane scanning mechanism for scanning an inner plane of the object to be examined with the object light, an objective lens, the two-splitting half mirror for combining the object light returning from the object to be examined with the reference light returning from the light delay mechanism, and a light detector for detecting interference light combined at the two-splitting half mirror;

[4] in an optical coherence tomography device according to [2] or [3], the light delay mechanism contains a plurality of pairs of mirrors each comprising a first mirror and a second mirror arranged on the surface of a rotation member, which is rotated at high speed, in a radial direction pattern in such a manner as to cause the light to be reflected in the tangential direction of the rotation member;

[5] in an optical coherence tomography device according to [2] or [3], the fixed mirror is a scanning-starting point adjusting mirror which can adjust the scanning-starting position in the depth direction so as to correspond to the Z direction, which is the depth direction of the optical axis of the object light; and

[6] in an optical coherence tomography device according to [3], the plane scanning mechanism has an X-axis scanning mirror and a Y-axis scanning mirror, and the plane (X-Y) of the object to be examined is scanned at high speed with the object light towards the object to be examined.

BEST MODE FOR CARRYING OUT THE INVENTION

Hereinafter, an embodiment of the present invention will be described in detail.

Figure 1:
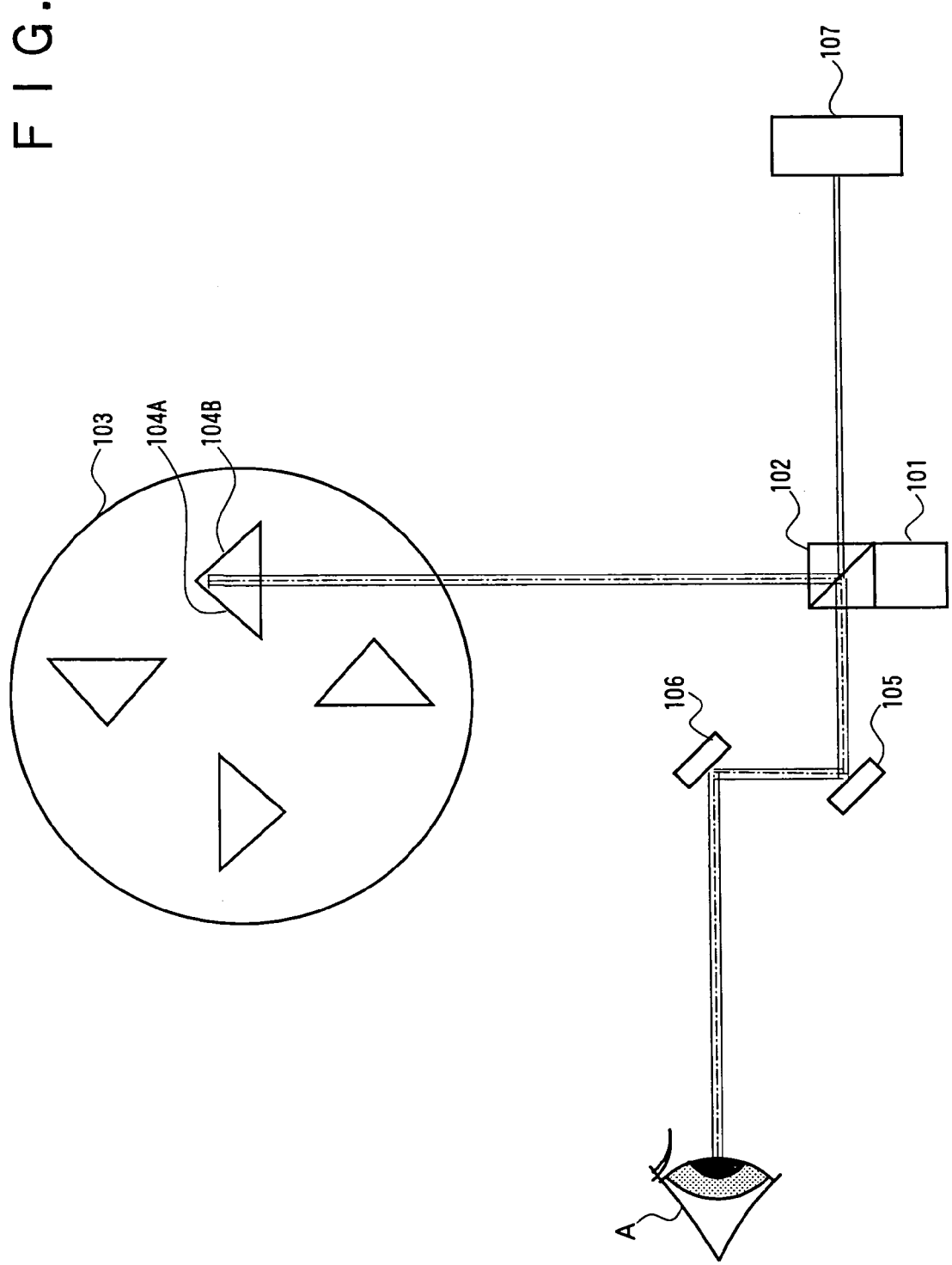
FIG. 1 shows the configuration of a conventional optical coherence tomography device.
Figure 2:
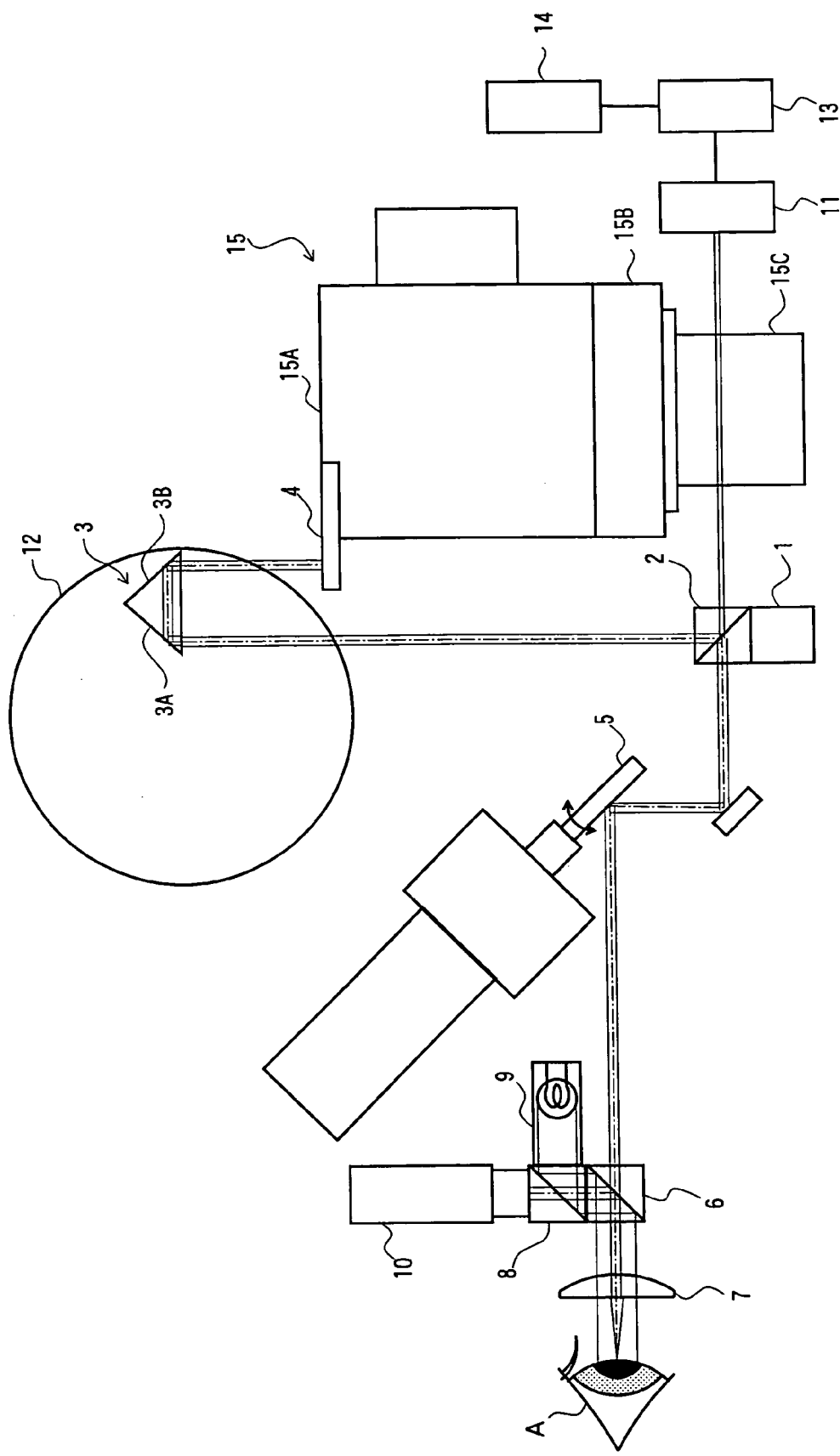
FIG. 2 shows the configuration of an optical coherence tomography device according to an embodiment of the present invention.

FIG. 2 shows the configuration of an optical coherence tomography device according to an embodiment of the present invention.

In FIG. 2, there are shown a low-coherence light source (e.g., an SLD (super luminescent diode) light source) 1, a half mirror (two-splitting half mirror) 2, a light delay mechanism 3, a first mirror 3A, a second mirror 3B, a scanning-starting point adjusting mirror (fixed mirror) 4, a plane scanning mechanism (X-axis scanning mirror and Y-axis scanning mirror) 5, a dichroic mirror 6 (reflecting visible light and transmitting infrared light), an objective lens 7, a half mirror 8 for a camera light source, a CCD illumination light source 9, a monitor CCD 10, a light detector 11, a rotation member 12, a PC (personal computer) 13, a display 14, a mechanism 15 for optionally moving the fixed mirror 4 in the optical-axial direction. The mechanism 15 comprises a single-axis translation stage mechanism 15A, a coupling mechanism 15B, and a pulse motor 15C. Reference letter A designates an object to be examined.

Light from the SLD light source 1, which is a low-coherence light source, is split by means of the half mirror 2 into object light towards the object A to be examined and also into reference light. The reference light, which is one of the two-split light beams, is guided to the first mirror 3A and the second mirror 3B, which are contained in the light delay mechanism 3, and the fixed mirror (scanning-starting point adjusting mirror) 4. The light is reflected at and returns from the fixed mirror 4 to the half mirror 2 via the same optical path.

On the other hand, the object light, which is the other of the two-split light beams, is guided through the plane scanning mechanism (X-axis scanning mirror and Y-axis scanning mirror) 5, the dichroic mirror 6, and the objective lens 7 to be made incident upon the object A to be examined. The reflected light is caused to return to the half mirror 2 via the same optical path.

In the light delay mechanism 3, a plurality of pairs of mirrors each comprising the first mirror 3A and the second mirror 3B are arranged on the rotation member 12, which is rotated at high speed, in a radial pattern in such a manner that the light is reflected in the tangential direction of the rotation member 12.

The rotation member 12 is rotated at high speed. When the reference light from the half mirror 2 propagates along the optical path from the half mirror 2, through the first mirror 3A, the second mirror 3B, the fixed mirror (scanning-starting point adjusting mirror) 4, the second mirror 3B and the first mirror 3A, to the half mirror 2, the first mirror 3A and the second mirror 3B move the optical path in the forward direction or in the backward direction due to the rotation of the rotation member 12. Thus, the reference light is Doppler-frequency shifted to the UV side or the infrared side. The above-described heterodyne interference beat signal is generated correspondingly to this Doppler-frequency shift.

With the above-described configuration, the length of the optical path can be optionally selected within the range where the reference light can be applied along the optical path as described above, and can be made to correspond to the object light in the depth direction (Z direction) of the optical axis. Thus, the reflection structure of a deep layer of the object A to be examined can be scanned in the depth direction.

Generally, in the plane scanning mechanism (X-axis scanning mirror and Y-axis scanning mirror) 5, the mirrors fixed to the rocking portions of devices named galvanometers, which carry out rocking-motion at high speed and with high accuracy, are arranged for the X-axis scanning and the Y-axis scanning, respectively. The galvanometers for the X- and Y-axis scanning are synchronously controlled, so that the X-Y plane is scanned with the object light reflected from the mirrors.

Substantially all of the light (infrared rays) from the SLD light source 1 is passed through the dichroic mirror 6 to propagate toward the object A to be examined. Substantially all of the light (visible light) from the CCD illumination light source 9 is reflected from the dichroic mirror 6 and propagate toward the object A to be examined. Moreover, of the light reflected from the object A to be examined, nearly all of the infrared rays (signal component) are passed through the dichroic mirror 6 to propagate toward the light detector 11. Of the light reflected from the object A to be examined, substantially all of the visible light (real picture component) is reflected from the dichroic mirror 6 to propagate toward the monitor CCD 10.

The half mirror 8 for the camera light source and the CCD illumination light source 9 are used to illuminate the object A to be examined when a real picture of the object A is taken by the monitor CCD 10.

The monitor CCD 10 captures the real picture of the object A to be examined.

The reference light and the object light returning to the half mirror 2 are combined with each other, and are supplied to the light detector 11. The reference light and the object light are combined to become interference light, due to the interference phenomena of light waves, so that beats are generated. In this case, when the length of the optical path from the half mirror 2 to the fixed mirror (scanning-starting point adjusting mirror) 4 is equal to the length of the optical path from the half mirror 2 to the object A to be examined, a heterodyne interference beat signal is generated in the combined interference light. The heterodyne interference beat signal is converted to an electrical signal in the light detector 11, and is supplied to the PC (personal computer) 13.

The PC 13 carries out three-dimensional image-processing of the heterodyne interference beat signal, and a cross-sectional picture of the object A to be examined is displayed on the display 14.

Referring to the first mirror 3A and the second mirror 3B, right-angle prisms, corner-cube reflectors for three-plane reflection, Littrow reflectors, and cat's eyes may be used, in addition to the surface-reflection mirrors arranged at a right-angle to each other, which is the simplest arrangement.

Moreover, a half-mirror may be installed in the optical path of the object light, and the real surface of the object A to be examined is imaged by means of an image pickup device such as a CCD device or the like. Thus, positioning of the optical axis for examination of the object A to be examined can be easily performed.

Moreover, a mechanism 15 for optionally moving the fixed mirror 4 in the optical-axis direction may be added, and thus, the scanning reference position in the depth direction (Z direction) can be optionally set.

As described above, according to the high-speed optical delay generating method in optical coherence tomography of the present invention, the reference light from the half mirror 2 propagates along the optical path from the half mirror 2, through the first mirror 3A, the second mirror 3B, the fixed mirror (scanning-starting point adjusting mirror) 4, the second mirror 3B and the first mirror 3A, to the half mirror 2. That is, the reference light moves along the same optical path when it is made incident and is reflected, and the light returns to the half mirror 2. Thus, the problem of the conventional high-speed optical delay generating method in optical coherence tomography, that is, the shift of the reflection optical axis from the incidence optical axis, does not occur. Thus, heterodyne interference beat signals combined at the half mirror 2 can be obtained at high speed over a very wide angular range.

Thus, according to the present invention, a cross-sectional picture with a sufficiently long scanning distance in the depth direction (Z direction) can be provided.

Moreover, according to the present invention, high-precision cross-sectional information can be taken at high speed over a wide angular range to be displayed. Thus, for example, when the present invention is applied to an ophthalmic disease diagnostic device, the diagnosis of eyegrounds, which has until now been conducted based on intuition and experience of ophthalmologists can be easily carried out at high speed and over a wide angular range.

Thus, eye-ground retinal diseases can be found early. Such diseases, which have been difficult to detect and cause the patients to lose their sight, can be treated early for healing. This significantly reduces the physical and mental burden of the patients.

The present invention is not restricted to the above-described embodiments. Different modifications can be made based on the spirit of the present invention. It is to be noted that these modifications should not be excluded from the present invention.

As described above in detail, according to the present invention, a cross-sectional picture having a sufficiently long scanning distance in the depth direction (Z direction) can be obtained at high speed. That is, the reference light from the half mirror returns along the same optical path for both of the incident light and the reflection light. Thus, shifting of the reflection optical axis to the incidence optical axis, which is a problem of the conventional high-speed delay generating method in optical coherence tomography, does not occur. Heterodyne interference beat signals combined at the half mirror can be obtained at high speed and over a wide angular range.

INDUSTRIAL APPLICABILITY

With the optical coherence tomography device of the present invention, high-precision cross-sectional information can be taken at high speed and over a wide angular range to be displayed. In particular, this device is suitable for use as a medical diagnostic device such as an ophthalmic disease diagnostic device.

The invention claimed is:

1. An optical coherence tomography device comprising:
   (a) a low-coherence light source;
   (b) a two-splitting half mirror configured to split light from the low-coherence light source into an object light towards an object to be examined and configured to split light from the low-coherence light source into a reference light;
   (c) a light delay mechanism configured to delay the reference light by a rotation reflector;
   (d) a scanning-starting point adjusting mirror configured to cause the reference light from the light delay mechanism to be reflected and returned to the delay mechanism;
   (e) a plane scanning mechanism configured to scan an inner plane of the object to be examined with the object light;
   (f) an objective lens;
   (g) the two-splitting half mirror configured to combine the object light returning from the object to be examined with the reference light returning from the light delay mechanism; and
   (h) a light detector configured to detect interference light combined at the two-splitting half mirror;
   (i) wherein the light delay mechanism includes a plurality of pairs of mirrors each comprising a first mirror and a second mirror arranged on the surface of a rotation member, which is rotated in a radial direction so as to cause the reference light to be reflected in a tangential direction of the rotation member;
   (j) wherein the scanning-starting point adjusting mirror is configured to adjust a scanning-starting point adjusting position in the depth direction so as to correspond to the Z direction, which is the depth direction of the optical axis of the object light; and
   (k) wherein the plane scanning mechanism has an x-axis scanning mirror and a y-axis scanning mirror, and the x-y plane of the object to be examined is scanned at high speed with the object light towards the object to be examined; and further comprising
   (l) a dichroic mirror configured to pass substantially all of the light from the low-coherence light source to the object to be examined and configured to reflect a second light from a second light source to a monitor.

2. An optical coherence tomography device according to claim 1, wherein the object to be examined is eyes.

3. An optical coherence tomography device according to claim 1, wherein the plane scanning mechanism is configured to scan an eye.

4. An optical coherence tomography device according to claim 1, wherein the second light source is a charge coupled device (CCD) light source.

5. An optical coherence tomography device according to claim 1, wherein the monitor is a charge coupled device (CCD) monitor.

6. An optical coherence tomography device according to claim 1, further comprising a half-mirror configured to split the second light from the second light source into a monitor light and a second object light so that the object to be examined is illuminated when a real picture of the object to be examined is taken by the monitor.

* * * * *